(12) United States Patent
Holmquist et al.

(10) Patent No.: US 7,592,432 B2
(45) Date of Patent: Sep. 22, 2009

(54) POLYPEPTIDE CLEAVAGE PROCESS

(75) Inventors: Barton Holmquist, Eagle, NE (US); Daniel Strydom, Lincoln, NE (US); Jin Seog Seo, Brampton (CA); Kirk Cryer, Madison, WI (US)

(73) Assignee: Restoragen, Inc., Lincoln, NE (US)

( * ) Notice: Subject to any disclaimer, the term of this patent is extended or adjusted under 35 U.S.C. 154(b) by 609 days.

(21) Appl. No.: 10/997,822

(22) Filed: Nov. 24, 2004

(65) Prior Publication Data

US 2005/0227314 A1    Oct. 13, 2005

Related U.S. Application Data

(63) Continuation of application No. PCT/US03/16647, filed on May 23, 2003.

(60) Provisional application No. 60/383,484, filed on May 24, 2002.

(51) Int. Cl.
*C08H 1/00*     (2006.01)
*C12N 1/20*     (2006.01)
*C12N 15/63*    (2006.01)

(52) U.S. Cl. .................. 530/402; 435/69.1; 435/252.1; 530/333

(58) Field of Classification Search .................. None
See application file for complete search history.

(56) References Cited

U.S. PATENT DOCUMENTS

| | | |
|---|---|---|
| 5,352,771 A | 10/1994 | Kostic et al. |
| 5,393,924 A | 2/1995 | Tafesh et al. |
| 5,457,066 A | 10/1995 | Frank et al. |
| 5,580,751 A | 12/1996 | Buchardt et al. |
| 6,660,758 B1 | 12/2003 | Nicolaou et al. |
| 6,660,763 B2 | 12/2003 | Tang et al. |
| 2005/0227313 A1* | 10/2005 | Seo et al. .................. 435/68.1 |
| 2005/0287632 A1* | 12/2005 | Holmquist et al. ......... 435/69.1 |

FOREIGN PATENT DOCUMENTS

WO    WO-2004011599 A2    2/2004

OTHER PUBLICATIONS

Parac et al., "New Regioselectivity in the Cleavage of Histidine-Containing Peptides by Palladium(II)Complexes Studied by Kinetic Experiments and Molecular Dynamics Simulations", J. Am. Chem. Soc. 121: 3127-3135 (1999).*
"International Search Report for Application No. PCT/US2003/16647", (Jul. 2, 2004), 2 Pages.
Dou, et al., "Preliminary Study On The Cleavage Of Chimeric protein GST-CMIV With Palladate (II) complex", Prep. Biochem & Biotechnol. 301 (1), (2000),69-78.
Drexler, C, et al., "Palladium (II) and platinum (II) complexes with 1,5-dithiacyclooctane(dtco)—structures of Pd(dtco)C12 and Pd(dtco2)(NO3)2 and kinetics of ligand substitution in [Pd(dtco2)]2plus by bidenate ligands", Inorganic Chemistry, 30c, (1991), 1297-1302.
Hohmann, H, et al., "Rate and equilibrium data for substitution reactions of diaqua(ethylenediamine)palladium(II) with chloride in aqueous solution", Inorg. Chim. Acta, 174(1), (1990),87-92.
Milovic, N, et al., "Interplay of Terminal Amino Group and Coordinating Side Chains in Directing Regioselective Cleavage of Natural Peptides and Protiens with Palladium(II) Complexes", Inorganic Chemistry, (Dec. 2002).
Rau, T, et al., "Complex Formation and Ligand Substitution Reactions of (2-Picolylamine)palladium(II) with Various Biologically Relevant Ligands. Characterization of (2-Picolylamine)(1,1-cyclobutanedicarboxylato)palladium(II)", Inorganic Chemistry, 36, (1997),1454-1463.
Zhu, L, et al., "Site-Specific Hydrolytic Cleavage of Cytochrome c and of Its Heme Undecapeptide, Promoted by", J Am Chem Soc, 116, Site-specific hydrolytic cleavage of cytochrome c and of Its heme undecapeptide, promoted by coordinated complexes of palladium (II),(1994),5218-5224.
"International Application No. PCT/US03/16647 International Preliminary Examination Report mailed Sep. 7, 2004", 8 pgs.
"U.S. Appl. No. 10/997,081 Response to Non-Final Office Action filed Sep. 4, 2007", 10 pgs.
"International Application No. PCT/US03/16648 International Preliminary Examination Report mailed Dec. 13, 2004", 4 pgs.
"International Application No. PCT/US03/16648 International Search Report mailed May 27, 2004", 6 pgs.
"International Application No. PCT/US03/16648 International Written Opinion mailed Sep. 7, 2004", 6 pgs.
"International Application No. PCT/US2003/016647 International Search Report mailed Jul. 2, 2004", 4 pgs.
"International Preliminary Examination Report dated Jan. 28, 2005 in Serial No. PCT/US03/16468", 4 pgs.
"International Search Report dated Jan. 15, 2004 in Serial No. PCT/US2003/016468", 3 pgs.
"International Written Opinion dated Oct. 7, 2004 in Serial No. PCT/US03/16468", 3 pgs.
"Non-Final Office Action mailed Oct. 9, 2007 in U.S. Appl. No. 11/997,762, 10 pages", 10.
"PCT Search Report in Application No. PCT/US03/16468", (Dec. 12, 2003).
Djuran, M. I., et al., "Hydrolysis of amide bond in histidine-containing peptides promoted by chelated amino acid palladium(II) complexes: dependence of hydrolytic pathway on the coordination modes of the peptides", Polyhedron, 18(27), (Sep. 14, 1999),3611-3616.
Milovic, N. M., et al., "Palladium(II) and platinum(II) complexes as synthetic peptidases", Met Ions Biol Syst., 38, (2001),145-186.
Milovic, N. M., et al., "Palladium(II) Complexes, as Synthetic Peptidases, Regioselectively Cleave the Second Peptide Bond "Upstream" from Methionine and Histidine Side Chains", Journal of the American Chemical Society, 124(17), (May 1, 2002),4759-4769.

(Continued)

Primary Examiner—Anand U Desai
(74) Attorney, Agent, or Firm—Campbell Nelson Whipps LLC (57) ABSTRACT

The invention provides a palladium-promoted hydrolytic polypeptide cleavage process which selectively cleaves the polypeptide at a Cys-His cleavage site comprising solubilizing the polypeptide in a reaction mixture comprised of a palladium promoter dissolved in a high-concentration formic acid, wherein the concentration of the formic acid in the reaction mixture is between about 1 to about 22 molar.

47 Claims, 6 Drawing Sheets

OTHER PUBLICATIONS

Parac, T. N., et al., "New Selectivity and Turnover in Peptide Hydrolysis by Metal Complexes. A Palladium(II) Aqua Complex Catalyzes Cleavage of Peptides Next to the Histidine Residue", *J. Am. Chem. Soc.*, 118(1), (1996),51-58.

Park, S. H., et al., "Role of proline, cysteine and a disulphide bridge in the structure and activity of the anti-microbial peptide gaegurin 5.", *Biochem. J.*, 368(Pt 1), (2002),171-182.

"U.S. Appl. No. 10/997,081, Final Office Action mailed Jan. 4, 2008", 8 pgs.

"U.S. Appl. No. 10/997,081, Notice of Allowance mailed Jun. 11, 2008", 8 pgs.

"U.S. Appl. No. 10/997,081, Response filed Feb. 23, 2007 to Restriction Requirement mailed Jan. 25, 2007", 8 pgs.

"U.S. Appl. No. 10/997,081, Restriction Requirement mailed Jan. 25, 2007", 5 pgs.

"U.S. Appl. No. 10/997,081 Non-Final Office Action mailed May 2, 2007", 6 pgs.

"U.S. Appl. No. 10/997,081 Response to Final Office Action filed Feb. 15, 2008", 10 pgs.

"U.S. Appl. No. 10/997,762, Advisory Action mailed Jul. 15, 2008", 7 pgs.

"U.S. Appl. No. 10/997,762, Final Office Action mailed Apr. 17, 2008", 9 pgs.

"U.S. Appl. No. 10/997,762, Response filed Jul. 17, 2007 to Restriction Requirement mailed Jun. 18, 2007", 14 pgs.

"U.S. Appl. No. 10/997,762, Response filed Jun. 17, 2008 to Final Office Action mailed Apr. 17, 2008", 14 pgs.

"U.S. Appl. No. 10/997,762, Restriction Requirement mailed Jun. 18, 2007", 5 pgs.

"U.S. Appl. No. 10/997,762 Response to Non-Final Office Action filed Jan. 9, 2008", 15 pgs.

"European Application Serial No. 03736710.9, European Office Action mailed Oct. 1, 2007", 6 pgs.

"International Application No. PCT/US03/16468, International Search Report Mailed Jan. 15, 2004", 1 pg.

"International Application Serial No. PCT/US03/16468, Written Opinion mailed Jan. 28, 2005", 4 pgs.

\* cited by examiner

[Pd(en)(OH$_2$)$_2$]$^{2+}$

[Pd(pn)(OH$_2$)$_2$]$^{2+}$

[Pd(pic)(OH$_2$)$_2$]$^{2+}$

[Pd(bp)(OH$_2$)$_2$]$^{2+}$

[Pd(phen)(OH$_2$)$_2$]$^{2+}$

[Pd(dtco-OH)(OH$_2$)$_2$]$^{2+}$

[Pd(OH$_2$)$_3$(OH)]$^{+}$

[PdCl$_4$]$^{2-}$

```
  1 ATGGCTAGCA TGACTGGTGG ACAGCAAATG GGTCGCGGAT CCGGCCAGGG   Frame 1
    M  A  S   M  T  G  G   Q  Q  M    G  R  G  S    G  Q  G 51 ACAGGCTCAA TATCTAGCGG CCTCCTTGGT TGTGTTCACC AACTACTCGG   Frame 1
    Q  A  Q   Y  L  A  A   S  L  V    V  F  T    N  Y  S  G 101 GCGACACGGC CAGCCAGGTG GACGTTAACG GTCCGCGTGC TATGGTCGAC   Frame 1
    D  T  A   S  Q  V    D  V  N  G   P  R  A    M  V  D 151 GACGACGACA AATGCCACTA CGCTGACGCT ATCTTCACCA ACTCTTACCG   Frame 1
    D  D  D  K   C  H  Y   A  D  A    I  F  T  N    S  Y  R 201 TAAAGTTCTG GGTCAGCTGT CTGCTCGTAA ACTGCTGCAG GACATCATGT   Frame 1
    K  V  L    G  Q  L  S   A  R  K   L  L  Q    D  I  M  S 251 CCCGTCAGCA GGGTGAATCT AACCAGGAAC GTGGTGCTCG TGCTCGTCTG   Frame 1
    R  Q  Q    G  E  S    N  Q  E  R   G  A  R    A  R  L 301 GCATAA
    A  *      Frame 1
```

Fig. 4

```
  1 ATGGCTAGCA TGACTGGTGG ACAGCAAATG GGTCGCGGAT CCGGCCAGGG   Frame 1
    M  A  S   M  T  G  G   Q  Q  M    G  R  G  S    G  Q  G 51 TCAGGCTCAA TATCTGGCTG CCTCCCTGGT TGTGTTCACC AACTACTCGG   Frame 1
    Q  A  Q   Y  L  A  A   S  L  V    V  F  T    N  Y  S  G 101 GCGACACGGC CAGCCAGGTG GACGTTAACC CGGAATTCTC TGTTGGTGGT   Frame 1
    D  T  A   S  Q  V    D  V  N  P   E  F  S    V  G  G 151 GGTGGTGGTC CGCGTTGCCA CTCTGTTTCT GAAATCCAGC TGATGCACAA   Frame 1
    G  G  G   P  R  C  H   S  V  S    E  I  Q  L    M  H  N 201 CCTGGGTAAA CACCTGAACT CTATGGAACG TGTTGAATGG CTGCGTAAAA   Frame 1
    L  G  K   H  L  N  S   M  E  R    V  E  W    L  R  K  K 251 AACTGCAGGA CGTTCACAAC TTCTAA   Frame 1
    L  Q  D   V  H  N    F  *
```

Fig. 5

```
  1 ATGGCTAGCA TGACTGGTGG ACAGCAAATG GGTCGCGGAT CCGGCCAGGG   Frame 1
    M  A  S  M  T  G  G  Q  Q  M  G  R  G  S  G  Q  G 51 ACAGGCTCAA TATCTAGCGG CCTCCTTGGT TGTGTTCACC AACTACTCGG   Frame 1
    Q  A  Q  Y  L  A  A  S  L  V  V  F  T  N  Y  S  G 101 GCGACACGGC CAGCCAGGTG GACGTTAACG GTCCGGCGTGC TATGGTCGAC   Frame 1
    D  T  A  S  Q  V  D  V  N  G  P  R  A  M  V  D 151 GACGACGACA AATGCCACTA CGCTGACGCT ATCTTCACCA ACTCTTACCG   Frame 1
    D  D  D  K  C  H  Y  A  D  A  I  F  T  N  S  Y  R 201 TAAAGTTCTG GGTCAGCTGT CTGCTCGTAA ACTGCTGCAG GACATCATGT   Frame 1
    K  V  L  G  Q  L  S  A  R  K  L  L  Q  D  I  M  S 251 CCCGTCAGCA GGGTGAATCT AACCAGGAAC GTGGTGCTCG TGCTCGTCTG   Frame 1
    R  Q  Q  G  E  S  N  Q  E  R  G  A  R  A  R  L 301 TGCCACTAA
    C  H  *   Frame 1
```

POLYPEPTIDE CLEAVAGE PROCESS

Cross-Reference to Related Applications

This application is a continuation under 35 U.S.C. 111(a) of PCT/US2003/016647, filed on May 23, 2003 and published on Feb. 5, 2004 as WO 2004/011599 A2, which claims priority under 35 U.S.C. 119(e) of U.S. Provisional Application No. 60/383484, filed on May 24, 2002, which applications and publication are incorporated herein by reference.

FIELD OF THE INVENTION

The invention provides highly specific, conformationally independent, palladate promoted hydrolytic cleavage of polypeptides, including relatively insoluble chimeric proteins in the form of inclusion bodies.

BACKGROUND OF THE INVENTION

It is well known that the production of peptides of less than about 100 amino acids in length by expression of peptide-encoding DNA in a recombinant host cell such as *E. coli* is plagued by enzymatic degradation of the expressed peptide within the host cell, which often results in partial or complete loss of the peptide. The most commonly employed means to overcome this problem is to insolubilize the peptide within the host cell. This can be affected by expressing the peptide as a chimeric protein in which the peptide is linked to a fusion partner. Normally, the fusion partner will be fused to the N-terminus of the peptide. The chimeric protein forms inclusion bodies within the cell, within which the peptide is protected from degradation by proteolytic enzymes. Once the inclusion bodies are recovered from the host cell, the peptide must be separated from the leader sequence, purified and recovered in an active form. Cleavage from the leader sequence may be accomplished by placing a sequence of amino acids at the junction of the leader and the peptide which are specifically recognized and cleaved under appropriate conditions, e.g. acid cleavage or enzymatic cleavage.

For example, introduction of acid-labile aspartyl-proline linkage between the two segments of a chimeric protein facilitates cleavage at low pH. This technique does not work if the product peptide, which is to be cleaved from the polypeptide, is not acid-labile. Chimeric proteins comprising hormones such as insulin and somatostatin have been cleaved with cyanogen bromide, which is specific for the carboxyl side of methionine residues. This method is not suitable when the product peptide contains methionine residues.

Cleavage of chimeric proteins by site-specific proteolysis has also been investigated. Chimeric proteins containing a chicken pro-alpha-2 collagen linker could be specifically degraded by purified microbial collagenase to release the components of the chimeric protein. Use of proteolytic enzymes is expensive, product peptide cleavage yield is frequently low, and it can prove difficult to separate the enzyme from a desired peptide product. Other methods for purification and recovery of a desired recombinant protein include construction of a poly-arginine tail at the C-terminus of the polypeptide. The arginine residues increase the overall basicity of the protein, which facilitates purification by ion exchange chromatography. Subsequent removal of the poly-arginine tail by carboxypeptidase B regenerates the desired protein and allows purification from basic contaminants due to the reduction in pI of the desired protein.

Acid cleavage can be accomplished by placing a specific dipeptide at the junction of the leader sequence and the peptide. Selection of the second amino acid will determine the rate at which the dipeptide bond is cleaved under acidic conditions. Of course, if the desired peptide contains any internal dipeptide sequences that are acid cleavable, then the cleavage site at the junction of the leader and the peptide must undergo acid cleavage at a substantially greater rate than the internal cleavage in order to avoid unacceptable loss of yield.

Zhu et al., *J. Am. Chem. Soc.*, 116: 5218 (1994), describe selective cleavage of cytochrome-c at S-hemo-Cysteinyl-Histidine (Cys(hemo)-His) using certain palladate(II)(Pd II) complexes under acidic conditions. Under the reaction conditions described in Zhu et al., cleavage of cytochrome c took 2 days at 40° C. and resulted in a cleavage yield of only 35-50%. (SDS-PAGE analysis in fact indicated some degree of non-specific cleavage; as the molar ratio of Pd to protein was increased from 1:1 to 4:1, there was an indication of cleavage at a site other than the Cys(hemo)-His sequence.)

Zhu et al. states at p. 5220 that 100 mM $HBF_4$, $HClO_4$, and $CF_3COOH$, or 70% formic acid, cleaved cytochrome-c. The reference thereafter concludes that cleavage was inhibited by the presence of chloride ions, a notable drawback as proteins purified from biological systems will almost invariably contain chloride ions. Notably, Zhu et al. at p. 5219 conclude that the rate of hydrolysis depended on conformational aspects of cytochrome c (i.e., cleavage was thought to be affected by the size of the cleaved peptide fragment and hence, the sequence of the polypeptide to be cleaved).

Dou, et al., "Preliminary Study On The Cleavage Of Chimeric protein GST-CMIV With Palladate(II) complex", *Prep. Biochem & Biotechnol.*, 301(1): 69-78 (2000) ("Dou, et al."), describe palladate promoted hydrolytic cleavage of a cecropin CMIV chimeric protein using formic acid, acetic acid, phosphoric acid and $HBF_4$ and $[Pd(en)(H_2O)_2]^{2+}$ Dou, et al. sought to cleave their chimeric protein specifically at two cleavage sites: Cys-His-Lys and Cys-His-Arg. According to Dou, et al., p. 76, only the $HBF_4$ reaction media cleaved the chimeric protein at the experimental conditions of 40° and reaction time of 48 hours. The cleavage in $HBF_4$ was said to be pH-dependent or independent depending on the amino acid adjacent to Cys-His: cleavage at Cys-His-Lys was pH-independent while cleavage at Cys-His-Arg was pH-dependent. Id. Further, cleavage at either site in $HBF_4$ was temperature dependent; when the temperature was increased to 60° C. the chimeric protein solubilized and it was no longer possible to cleave selectively. Id. Dou, et al. understood that their reaction would be strongly inhibited by the presence of chloride ions and employed an extra ion-exchange chromatography purification step before the cleavage reaction Read in context, Dou et al. and Zhu et al. would suggest that palladate promoted hydrolytic cleavage of polypeptides is not assured in concentrated acidic organic media, but instead is dependent upon the sequence of the polypeptide to be cleaved, reaction temperature and the possible inhibitory effects of chloride-containing species, including highly useful chloride-containing palladates. Dou et al. imply that solubilization of their chimeric protein results in a loss of cleavage specificity.

In sum, known hydrolytic polypeptide cleavage processes would suggest that even in concentrated acidic media, either the sequence of the polypeptide, the reaction media temperature or ionic species present in the reaction media could limit cleavage yield and specificity.

OBJECTS OF THE INVENTION

It is an object of the instant invention to provide an improved process for the hydrolytic cleavage of polypeptides.

It is an additional object of the instant invention to provide an improved process for the hydrolytic cleavage of polypeptides which is highly specific and which is not affected by the polypeptide sequence or the size of the cleaved peptide product.

It is an additional object of the instant invention to provide an improved process for the hydrolytic cleavage of polypeptides that have been expressed recombinantly in the form of chimeric proteins, especially chimeric proteins in the form of relatively insoluble inclusion bodies.

It is a still further object of the instant invention to provide an improved process for the hydrolytic cleavage of polypeptides, which is highly specific, which does not generate, unwanted side-products and which uses chloride-containing palladium species.

SUMMARY OF THE INVENTION

In accordance with the above-stated objects, the process of the instant invention provides a highly site-specific process for palladium-promoted hydrolytic cleavage of polypeptides under reaction conditions that are relatively insensitive to variations in reactant concentration, temperature or pH. The process is conformationally and sequence-independent, i.e., it achieves high cleavage yield irrespective of the type of amino acid groups adjacent to the specified cleavage site. Further, the process of the instant invention cleaves polypeptides under conditions which limit the formation of unwanted side-products and which enable the use of chloride-containing catalysts and reaction-media. The process may be employed to cleave, with a high degree of specificity, a single-copy recombinant polypeptide, a multi-copy recombinant polypeptide or a single or multi-copy recombinant chimeric protein construct. Consequently, the process can produce numerous cleaved peptide fragments suitable for further processing.

More specifically, the invention provides a process for cleaving a polypeptide at a Cys-His cleavage site in a reaction medium comprising concentrated formic acid and a palladate promotor. In one embodiment, a chimeric protein comprised of a leader sequence joined by a Cys-His cleavage site to the N-terminus of the peptide is cleaved by solubilizing the chimeric protein in a reaction mixture comprised of a palladium promotor dissolved in a high-concentration formic acid, wherein the concentration of the formic acid in the reaction mixture is between about 1 to about 22 molar. These reaction media solubilize chimeric proteins or inclusion bodies previously considered to be relatively insoluble and such solubilization, rather than decreasing the specificity of cleavage, actually leads to improved yields of cleaved peptide. Importantly, the process cleaves such chimeric proteins in a manner that facilitates additional processing necessary to post-translationally modify the cleaved peptide, e.g., amidation.

In one embodiment, the invention provides a process for preparing a peptide by cleaving a chimeric protein which is comprised of a leader. sequence joined by a Cys-His cleavage site to the N-terminus of the peptide by solubilizing and reacting the protein in a reaction mixture comprising a high concentration of formic acid solvent and a palladium promotor, wherein the concentration of the formic acid in the reaction mixture is between about 13 to about 22 molar.

In preferred embodiments of the process of the instant invention (i) the molar ratio of palladium promotor to chimeric protein in the reaction mixture is from about 2:1 to about 20:1, (ii) the reaction mixture temperature is maintained at about 50° C. to about 70° C.; and (iii) the peptide is recovered from the reaction mixture in a substantially formylated form which is deformylated in a second hydrolytic step removing formic acid from the cleavage reaction product by reacting the cleaved and formylated peptide with a nucleophile such as 150 mM glycine, or 25 mM hydroxylamine, at a pH in the range of 6 to 9 or by incubating the formylated product in dilute acid for 4 to 16 hours.

Palladium promoted acid cleavage in accordance with the process of the instant invention is facilitated by the use of these high concentrations of formic acid which solubilizes inclusion bodies such as T7tag-Vg-$D_4$K-CH-GRF(1-44)-Ala (SEQ ID NO:2), T7tag-Vg-$D_4$K-CH-GRF(1-44)-CH (SEQ ID NO:6) or T7tag-Vg-$G_5$PR-CH-PTH(1-34) (SEQ ID NO:4).

DETAILED DESCRIPTION OF THE INVENTION

It will be appreciated that the process of the instant invention may be employed to cleave naturally occurring peptides, synthetically derived peptides, and recombinantly derived peptides. The embodiments described in detail hereinafter relate to cleavage of recombinantly expressed chimeric proteins in the form of inclusion bodies.

The process of the instant invention can be applied to cleave chimeric proteins which have been recombinantly expressed in a microbial host cell using known techniques of recombinant DNA production and which have been recovered from the host cell in the form of an inclusion body. Any suitable host cell known to be useful for the expression of proteins by recombinant DNA methods may be employed to express such chimeric proteins, including prokaryotic and eukaryotic host cells and cell lines. *E. coli* is a preferred host cell. The host cell contains an expression vector which encodes the chimeric protein under the control of a regulatory sequence which is capable of directing its expression in the host, as well as an origin of replication that is functional in the host cell. The vector may contain other DNA sequences conventionally employed in recombinant DNA technology such as sequences encoding selectable markers. Methods for expressing a foreign gene in a host organism also are well known in the art (see, e.g., Maniatis et al. *Molecular Cloning: A Laboratory Manual,* Cold Spring Harbor Laboratory Press, $2^{nd}$ ed., 1989).

The gene encoding a particular polypeptide can be constructed by chemically synthesizing the entire nucleotide sequence, by amplification, such as by the polymerase chain reaction (PCR), or by cloning the gene of interest. The gene is then subcloned into an appropriate expression vector. Cloning vectors, expression vectors, plasmids, and viral vectors are well known in the art (see, e.g., Maniatis et al., supra, and Goedell, *Methods in Enzymology Vol.* 185 (Academic Press 1990)). Example 1 provides a description of the preparation of a T7-based expression system useful for high-level expression of mammalian proteins in *E. coli.*

The host cell containing the expression vector is grown and the chimeric protein expressed under appropriate conditions. The conditions for growth of the host cell and expression of the chimeric protein will vary depending on various factors such as the host cell employed, the promoter and the particular chimeric protein being expressed. Those skilled in the art are capable of determining the appropriate conditions for the particular host/vector system employed. Methods for expressing a foreign gene in a host organism also are well known in the art (see, e.g., Maniatis et al. *Molecular Cloning: A Laboratory Manual*, Cold Spring Harbor Laboratory Press, $2^{nd}$ ed., 1989). The gene encoding a particular polypeptide can be constructed by chemically synthesizing the entire nucleotide sequence, by amplification, such as by the polymerase chain reaction (PCR), or by cloning the gene of interest. The gene is then subcloned into an appropriate expression vector. Cloning vectors, expression vectors, plasmids, and viral vectors are well known in the art (see, e.g., Maniatis et al., supra, and Goedell, *Methods in Enzymology, Vol.* 185 (Academic Press 1990)). Example 1 provides a detailed description of the preparation of a T7-based expression system useful for high-level expression of mammalian proteins in *E. coli.*

When a polypeptide is prepared by recombinant techniques, one can add a Cys-His cleavage site within the sequence of the polypeptide by incorporating or mutating the appropriate nucleotides into the encoding nucleic acid by any of various methods including, for example, site-directed mutagenesis. Such a Cys-His sequence can provide a site for cleavage by palladium complexes as described herein. Recombinant methods can also be used to generate a nucleic acid encoding a protein with a repeating polypeptide sequence, each sequence separated by a Cys-His cleavage site. In this case, palladium complex-promoted cleavage can occur at multiple Cys-His sites in the polypeptide, releasing multiple copies of the desired peptide.

Application of the process of the instant invention to peptides or proteins that contain a Cys-His sequence results in selective cleavage at the Cys-His sequence. Alternatively, to facilitate cleavage, a Cys or a His residue may be incorporated into a site adjacent to the residue present in a peptide to create a Cys-His cleavage site, e.g., by site-specific mutagenesis. Thus, selective cleavage can then be achieved at the incorporated Cys-His site to produce peptide fragments. In the rare case in which a desired peptide or protein contains an intrinsic Cys-His sequence where palladium-promoted cleavage would cleave the peptide or protein into undesired fragments, site-specific mutagenesis could be used to alter either the Cys or the His residue to another amino acid to prevent cleavage.

Thus, the process of the instant invention provides for the cleavage of chimeric proteins comprising peptides which include, but are not limited to, the glucagon-like peptide-1 (GLP-1), glucagon-like peptide-2 (GLP-2), parathyroid hormone (PTH), parathyroid hormone related protein, growth hormone releasing hormone (GRF), adrenocorticotropic hormone (ACT), enkephalins, endorphins, exendins, amylins, various opioid peptides, frog skin antibiotic peptides, such as gaegurins 5 and 6, brevinin 1, the ranatuerins 1 through 9, and the esculetins, glucose-dependent insulinotropic polypeptide (GIP), glucagon, motilin, thymopoietins, thymosins, ubiquitin, serum thymic factor, thymic humoral factor, neurotensin, tuftsin, and fragments and derivatives of these peptides.

Many polypeptides have an amide at their C-terminal and/or an —S—S-linkage in the molecule. The precursor non-amidated or reduced forms of these peptides, respectively, can be expressed as a fusion construct with a Cys-His cleavage site incorporated and subjected to cleavage by palladium complexes in accordance with the process of the instant invention. The product can then be amidated or oxidized to produce the final desired molecule. Examples of such peptides include gastrin, calcitonin, luteinizing-hormone-releasing hormone, pancreatic polypeptide, endothelin, corticotropin releasing factor, neuropeptide Y, atrial naturetic peptide, amylin, galanin, somatostatins, vasoactive intestinal peptide, insulin, and fragments and derivatives of these peptides.

Examples of leader sequences which can be employed with chimeric proteins include a signal sequence such as that used to direct secretion of a protein from a cell, the N-terminal portion of a mature protein sequence, such as from a structural gene, a linker sequence, or combinations thereof.

In preferred embodiments of the instant invention, the chimeric protein has a molecular weight of between about 400 to about 100,000 daltons, or more preferably between 1,000 and 50,000 daltons and can comprise any of the natural amino acids, such as Ala (A), Arg (R), Asp (D), Asn (N), Glu (E), Gln (Q), Gly (G), His (H), Leu (L), Ile (I), Lys (K), Met (M), Cys (C), Phe (P), Pro (P), Ser (S), Thr (T), Trp (W), Tyr (Y), Val (V) (single letter amino acid code in parentheses), or may comprise any side chain-modified amino acid derivative commonly used in peptide chemistry. The latter amino acid derivatives include, for example, nipecotic acid, 1- or 2-napthylalanines and p-benzoylamino-L-phenylalanine, among others.

Inclusion bodies can be recovered from the host cells by known methods such as, for example, lysing the cells chemically or mechanically and separating the inclusion bodies (chimeric protein) by centrifugation.

Cleavage is usually carried out at a temperature of between about 50° C. to about 70° C.

It is understood that the reaction conditions of the cleavage step of the process of the instant invention are adjusted depending on the palladium complex used and the characteristics of the polyp eptide to be cleaved. The palladium complex should be solubilized, which will affect the reaction conditions. Moreover, in a preferred embodiment, the reaction conditions used will at least partially denature the polypeptide to be cleaved.

Palladium (Pd) (II) complexes that can promote the cleavage of polypeptides in accordance with the instant invention include $[Pd(OH_2)_3(OH)]^+$, $[PdCl_4]^{2-}$, cis-$[Pd(en)(OH_2)_2]^{2+}$, cis-$[Pd(Pn)(OH_2)_2]^{2+}$, cis-$[Pd(pic)(OH_2)_2]^{2+}$, cis-$[Pd(bpy)(OH_2)_2]^{2+}$, cis-$[Pd(phen)(OH_2)_2]^{2+}$, and cis-$[Pd(dtco-OH)(OH_2)2]^{2+}$. Additionally, Pd (IV) complexed with chloride ion as hexachloropalladate can also provide an effective cleavage agent. Palladium complexes can be prepared by methods well known in the art (see e.g., (H. Hohmann et al., *Inorg. Chim. Acta,* 174: 87 (1990); T. Rau et al., *Inorg. Chem.,* 36: 1454 (1997); C. Drexler et al., *Inorg. Chem.,* 30: 1297 (1991), or U.S. Pat. No. 5,352,771) or can be purchased commercially. Preferred palladium complexes include salts of the following: $[PdCl_4]^{2-}$, $[Pd(NCCH_3)_2(OH_2)_2]^{2+}$, $[PdCl_6]^{2-}$, $[Pd(dppe)(OH_2)_2]^{2+}$, $[Pd(tpp)(OH_2)_2]^{2+}$, and $[Pd(dppf)(OH_2)_2]^{2+}$. Palladium complexes most preferred include $[PdCl_4]^{2-}$, $[Pd(NCCH_3)(OH_2)_2]^{2+}$, and $[PdCl_6]^{2-}$. Complexes are used the salt of an inorganic base, such as sodium or potassium. The sodium and potassium salts of

Figure 1:
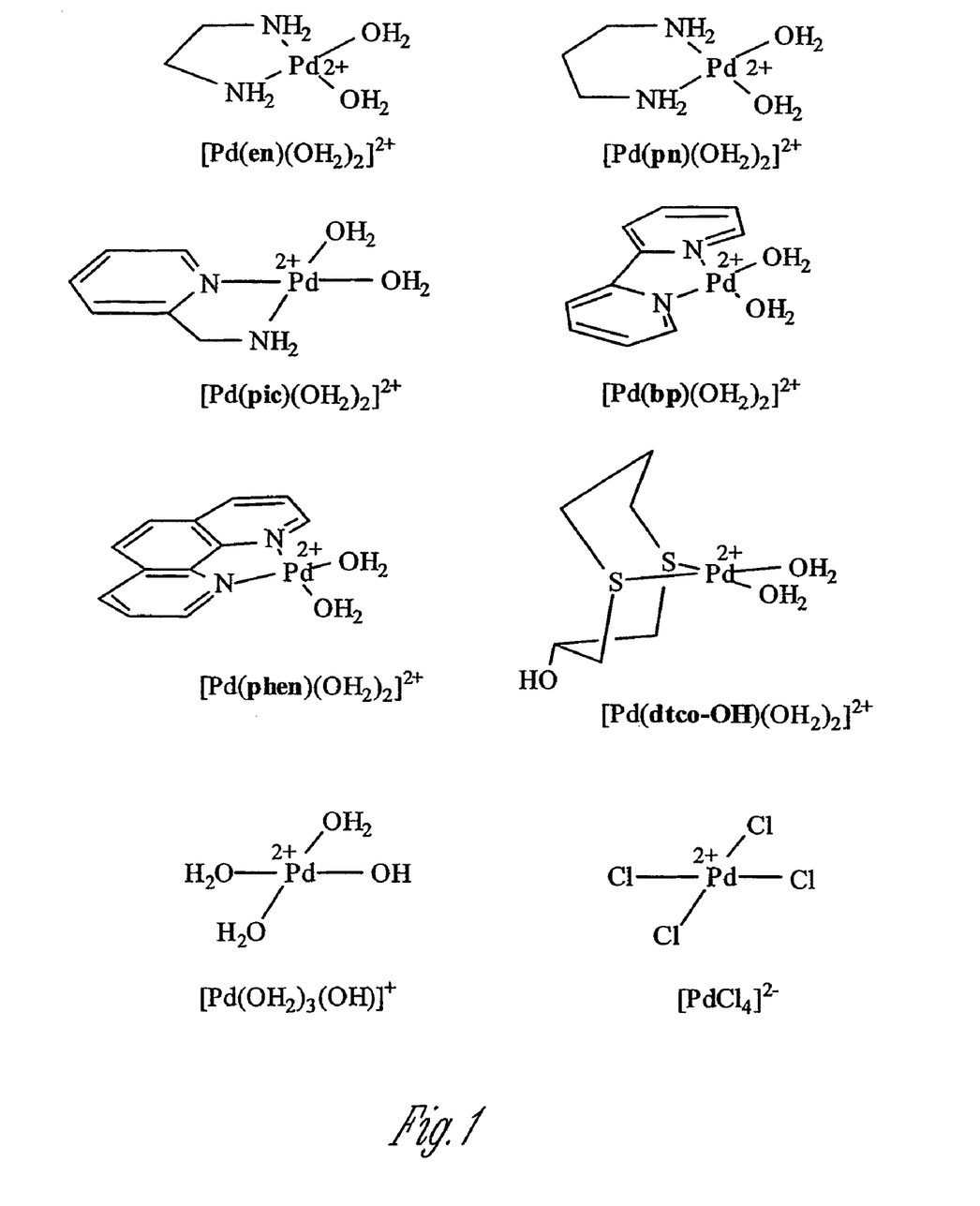
FIG. 1 illustrates the chemical structure of various palladium complexes useful in the process of the instant invention.

[PdCl$_4$]$^{2-}$ are preferred. Selected examples of the coordination structures of palladium complexes are shown in FIG. 1.

In the process of the instant invention, cleavage of the chimeric protein at the Cys-His site occurs at the carboxamide bond between the histidine residue and the residue immediately adjacent to the histidine on the C-terminal side. For example, the peptide NH$_2$-Ala-Ala-Cys-His-Gly-Gly-Gly-COOH (SEQ ID NO:7) would be cleaved as follows: NH$_2$-Ala-Ala-Cys-His-Gly-Gly-Gly-COOH (SEQ ID NO:7)+palladium complex→NH$_2$-Ala-Ala-Cys-His-COOH (SEQ ID NO:8) (Peptides are designated herein by amino acid abbreviations and are written so that going from left to right the N-terminal amino acid is on the left and the C-terminal amino acid is on the right, e.g. NH$_2$-Ala-Ala-Cys-His-Gly-Gly-Gly-COOH (SEQ ID NO:7)). The cleaved peptide produced in accordance with the process of the instant invention can be recovered from its fusion partner by ultrafiltration, precipitation, or more preferably, by reverse phase chromatography. Any commercially available reverse phase column suitable for the peptide being isolated may be employed. In many cases, the peptide recovered from the reverse phase column will refold into its native conformation, however, additional steps (e.g., oxidation) may be required to restore the peptide to a biologically active form, particularly when the peptide requires the formation of internal disulfide bonds for activity.

If desired, further purification steps can be employed using techniques known to those skilled in the art. Such steps may include, for example, HPLC, such as RP-HPLC or ion exchange chromatography steps.

In accordance with the process of the instant invention, the chimeric proteins T7tag-Vg-D$_4$KCH-GRF (1-44)-Ala (SEQ ID NO:2), T7tag-Vg-D$_4$K-CH-GRF(1-44)-CH (SEQ ID NO:6) and T7tag-Vg-G$_5$PR-CH-PTH (1-34) (SEQ ID NO:4) were expressed in *E. coli* and were thereafter isolated in the form of an inclusion bodies. This chimeric protein has a leader sequence connected by a cystinyl (Cys)-histidine (His) sequence to the growth hormone releasing factor peptide (GRF(1-44)CH). T7tag-Vg-D$_4$K-CH-GRF(1-44)-CH (SEQ ID NO:6), comprised a 14-residue signal sequence followed by both a 27 residue vestigial (Vg) sequence (which induced inclusion body formation and high expression) and a 13-residue linker which contained the Cys-His cleavage site. The T7tag-Vg-D$_4$K-CH-GRF(1-44)-Ala (SEQ ID NO:2) has a similar composition except that on palladium complex promoted cleavage the product is the growth hormone releasing factor analog GRF-Ala and finally, the T7tag-Vg-G$_5$PR-CH-PTH(1-34) (SEQ ID NO:4) is of similar construction and palladium promoted cleavage provides PTH(1-34), the natural hormone.

The isolated inclusion bodies were subjected to palladium-promoted acidic cleavage by (i) solubilizing them in a reaction mixture comprised of 80% formic acid, and (ii) addition of tetrachloropalladate in a 10:1 molar ratio of chimeric protein (inclusion body) to tetrachloropalladate. The cleavage reactions proceeded for between 1 to 24 hours, typically for about 1 to 6 hours, at a temperature ranging from about 50° C. to about 70° C. In some instances, ethylenediamine, picolyl amine (2-aminomethyl pyridine or "pic"); methionine, or histidine were added to the reaction mixture to increase yield.

Under these conditions, yields of around 75% of substantially formylated peptide were obtained in around two hours using formic acid; around 95% of this formylated peptide was deformylated in accordance with the process of the instant invention by removing the formic acid, and incubating the formylated peptide in 150 mM glycine and 25 mM hydroxylamine at pH 8.5 or incubating the formylated peptide in dilute acid for up to 16 hours. Alternately, the reaction mixture in formic acid was diluted up to 10 fold with dilute acid and held at about 15 to 30° C. for up to 16 hours, to achieve deformylation of the formylated peptide.

Other embodiments of the instant invention are disclosed in the following Examples, which are illustrative and not limiting.

EXAMPLE 1

Preparation of GRF(1-44)Ala

1. Preparation of Palladium Cleavage Promoters p Palladium(II) complexes were prepared as follows. Na$_2$PdCl$_4$, cis-[Pd(en)Cl$_2$], cis-[Pd(bp)Cl$_2$] and cis-[Pd(phen)Cl$_2$] were purchased from Aldrich Chemical Co. and Strem Chemical Co. cis-[Pd(pn)Cl$_2$] (H. Hohmann et al., *Inorg. Chim. Acta*, 174: 87 (1990)), cis-[Pd(pic)Cl$_2$] (T. Rau et al., *Inorg. Chem.*, 36: 1454 (1997)) and cis-[Pd(dtco-OH)Cl$_2$] (C. Drexler et al., *Inorg. Chem.*, 30: 1297 (1991)) were prepared essentially as described in the references. The complexes with aqua ligands, cis-[Pd(en)(OH$_2$)$_2$]$^{2+}$, cis-[Pd(pn)(OH$_2$)$_2$]$^{2+}$, cis-[Pd(pic)(OH$_2$)$_2$]$^{2+}$, cis-[Pd(bp)(OH$_2$)$_2$]$^{2+}$, cis-[Pd(Phen)(OH$_2$)$_2$]$^{2+}$, and cis-[Pd(dtco-OH)(OH$_2$)$_2$]$^{2+}$, were obtained as the nitrate salt by treating each corresponding complex with 1.98 equivalents of AgNO$_3$ in water. The complex [Pd(OH$_2$)$_3$(OH)](NO$_3$) in solution was obtained by stirring a mixture of K$_2$PdCl$_4$ and 3.98 equivalents of AgNO$_3$ for 2 hr at 50° C.

Solid samples of palladium (II) or (IV) complexes were solubilized in an appropriate aqueous solvent In reactions containing urea, the pH of the reaction following addition of the palladium complex was adjusted to 1.5 or 1.74, as indicated, by addition of trifluoroacetic or hydrochloric acid. The aqua complexes in solution were characterized by UV/vis spectroscopy.

2. Preparation of Polyeptide for Cleavage

Figure 4:
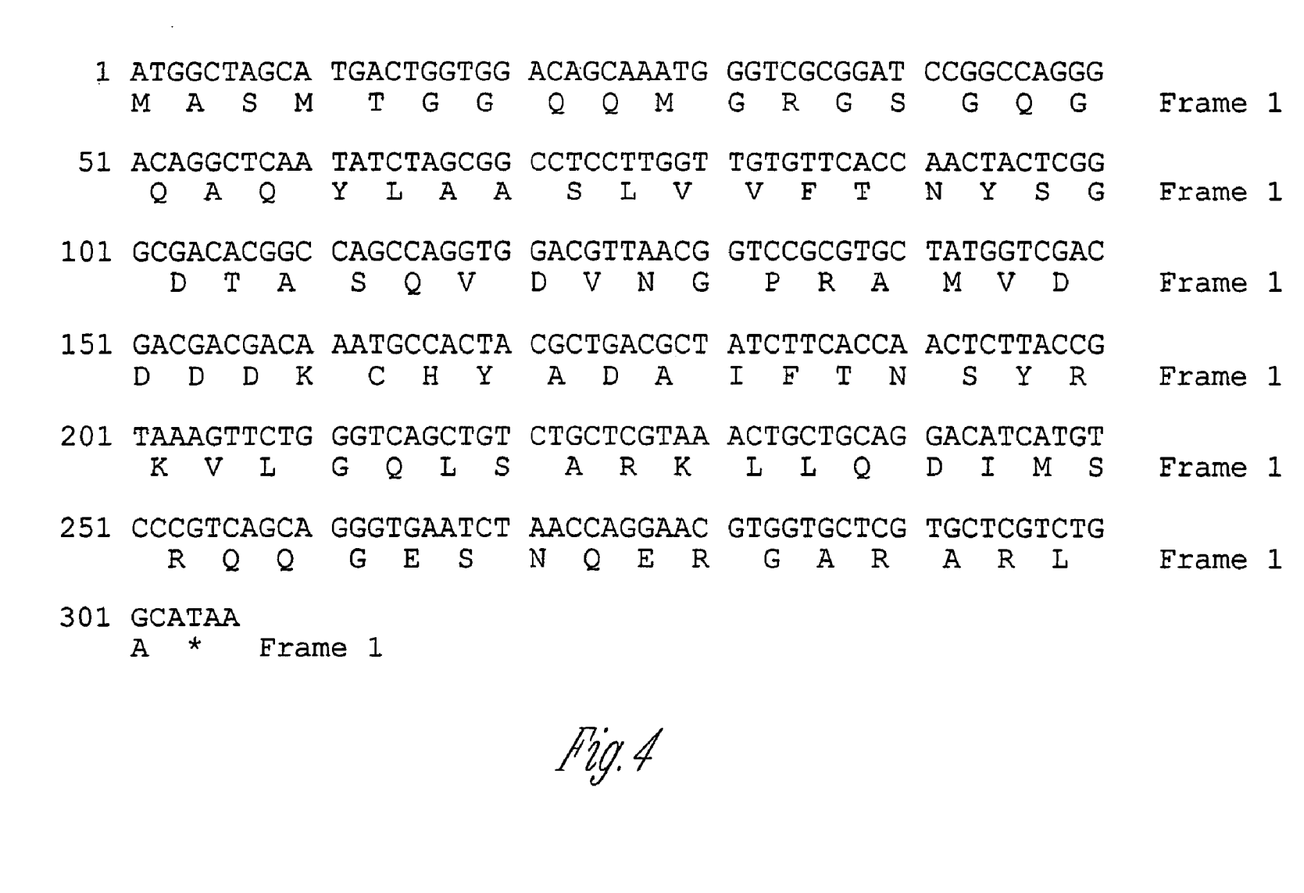
FIG. 4 illustrates the nucleotide (SEQ ID NO:1) and amino acid (SEQ ID NO:2) sequences of the chimeric protein T7tag-Vg-$D_4$K-CH-GRF(1-44)-Ala

Briefly, bacteria containing the expression plasmid encoding the leader-CH-GRF(1-44)-Ala polypeptide (FIG. 4) were grown in 500 mL shake flasks containing tryptone, yeast, glucose, batch salts (sodium and potassium mono- and diphosphate salts and ammonium sulfate), and antibiotic. Inoculated shake flasks were subject to orbital shaking (200 rpm, 37° C.). Incubation was completed when the culture reached an optical density (OD) of 0.8-1.8 at 540 nm.

Fermentors ranging from 5 L to 100 L production capacities were seeded using shake flask cultures. The media included batch salts, glucose, and chelated metals solution (potassium citrate, sodium citrate, magnesium sulfate, phosphoric acid ferric chloride, zinc chloride, cobalt chloride, sodium molybdate, manganese chloride, calcium chloride, and copper sulfate). The pH of the medium was adjusted to 6.9 prior to inoculation and the pH was maintained at 6.9 during culture. Dissolved oxygen was maintained at approximately 40%, via agitation and supplemental oxygen. Either silicone-based or polypropylene glycol-based "antifoam" was added aseptically on an "as needed" basis to reduce foaming in the fermentation culture.

When the fermentation culture OD reached 25 at 540 nm, recombinant protein expression was induced by adding filter-sterilized isopropylthiogalactoside (IPTG, 600 mM) to a final concentration of 0.5 mM, followed by filter-sterilized magnesium induction supplement (potassium citrate and magnesium sulfate). The culture was incubated for another 6 hr, and then cooled to 10-15° C.

Production fermentor cells were harvested from the fermentation broth by centrifugation. Cell pellets were pooled, resuspended in an appropriate volume (for example, 2 L lysis buffer for material from a 5 L fermentor) of lysis buffer (6 g Tris free base and 0.93 g EDTA in 993 g water), and lysed in a high-pressure homogenizer.

Cell solids and peptide precursor-containing inclusion bodies were pelleted by centrifugation, collected, and dissolved via homogenization in 1.5 M citric acid/1.0 mM EDTA solution, pH approximately 1.0 (for example, 1.5 L solution for material from a 5 L fermentor). The pH of this suspension was adjusted to 4.9 by slow addition of 10 M sodium hydroxide with continuous mixing, while maintaining the temperature at less than 15° C. The precipitate containing the GRF precursor peptide was collected by centrifugation and washed twice by resuspending in water and centrifuging to a pellet.

3. Cleavage of the Leader-CH-GRF(1-44)-Ala from the Chimeric Protein-Containing Inclusion Bodies Using Palladium Complexes.

Cleavage reactions were performed at a 10:1 molar ratio of palladium complex to solubilized peptide. In general, cleavage reactions can be performed at ratios of about 1:1 to about 20:1 (palladium complex:peptide). The purified peptide precursor precipitate (described above) was added to a solution of between 60 to 80% formic acid, at a ratio of 1 g of paste per 50 mL formic acid, and homogenized under high shear. The solution was transferred into an appropriately sized reaction vessel and immediately blanketed with argon gas. The solution was heated to 60° C. for approximately 1 hr and an aqueous solution of sodium tetrachloropalladate (6 mM) was added to achieve a 10:1 molar ratio of palladium complex to peptide. The reaction solution was incubated with stirring at 60° C. for 2 hr to effect cleavage of GRF(1-44)-Ala from the chimeric protein. The reaction solution was cooled to 20° C. and diluted to 6 fold of the original volume with cleavage diluent (0.6 M NaCl, 10 mM sodium thiocyanate) and incubated at ambient temperature under argon for 30 min to stop the reaction and to allow precipitation of undesired peptides and remaining inclusion bodies. The suspension was then filtered through a 0.45 μm filter. Reactions can also be stopped by methods well known in the art including, for example, column chromatography, evaporation, and freezing.

4. Isolation and Characterization of GRF(1-44)-Ala

The filtrate from the above step was subjected to Amberchrome CG-71 reversed-phase chromatography to separate cleaved GRF(1-44)-Ala peptide from leader and linker peptides, sodium thiocyanate, other contaminating proteins, residual palladium, and formic acid. The crude GRF(1-44)-Ala solution was loaded at 12-35 mg peptide per mL resin onto an Amberchrome CG-71 column, previously equilibrated in Buffer A (5% ethanol, 5 mM HCl), and washed with 7-11 column volumes of 5 mM HCl, to remove unbound material. Crude GRF(1-44)-Ala peptide was then eluted with a linear gradient set from 0 to 100% Buffer B (95% ethanol, 5 mM HCl) over 3 column volumes. Collection of the GRF (1-44)-Ala peak started when the peptide absorbance (at 280 μm) began to rise; the peak of interest eluted as a split peak at about 40% Buffer B and continued on the backside of the second peak until the absorbance leveled off.

Deformylation of formylated Ser and Thr residues in the crude GRF(1-44)-Ala pool from the Amberchrome column was accomplished by diluting the GRF(1-44)-Ala solution with 3 volumes of aqueous 8 M urea; glycine was then added to 0.048 M and the pH was adjusted to pH 9.0 with NaOH. The mixture was stirred for 30 min at 23° C. Following deformylation, the pH of the GRF(1-44)-Ala peptide product solution was adjusted to 7.0 with HCl, and filtered through a 0.45 μm filter.

The product GRF(1-44)-Ala peptide from the above filtration exhibited a single major peak on analytical reversed-phase HPLC. Mass spectroscopy of the HPLC peak gave the expected mass of GRF(1-44)-Ala. Orthogonal HPLC characterization of the GRF(1-44)-Ala product also was used to establish the identity of the product as GRF(1-44)-Ala. A Microsorb-MV Cyano C8 reversed-phase column was equilibrated with 5% acetonitrile and 0.1% trifluoroacetic acid (TFA). A multi-step gradient (from 20-40% buffer B) was used to isolate the GRF(1-44)-Ala product peak present following deformylation. The buffer system was composed of Buffer A (5% acetonitrile, 0.1% TFA) and Buffer B (95% acetonitrile, 0.1% TFA). Eluted sample peaks were identified by absorbance at 214 nm. Test samples were run in triplicate, and the average area under the eluted product peak was compared to the peak area from a similarly detected triplicate series of a GRF reference concentration standard (1.00±0.25 mg/mL). The concentration of GRF(1-44)-Ala was then calculated by comparison with the peak area of the reference standard. A single major peptide peak was observed for the deformylated-GRF(1-44)-Ala in the orthogonal HPLC system.

An amino acid composition analysis of the deformyliated GRF(1-44)-Ala cleavage product was determined and found to reflect the composition of the sequence.

The deformylated GRF(1-44)-Ala cleavage product was transamidated in accordance with the process of U.S. Pat. No. 5,580,751. The resultant putative GRF(1-44)amide was sequenced by Edman degradation and was found to have the amino acid sequence expected for GRF(1-44)amide, thereby confirming that deformylation was essentially complete.

5. Yield of Palladium (Palladate) Cleavage of Purified Chimeric Protein Containing GRF(1-44)-Ala.

The results of cleaving GRF(1-44)-Ala from the chimeric protein in the above process with various palladium complexes under various conditions are shown in Table 1. Generally, yields of the cleavage product ranged from 40 to 80% for most complexes with incubation periods of 6 hr or less. $Na_2PdCl_4$ was one of the more effective reagents, achieving approximately 70% cleavage in 80% formic acid in 1.7 hr.

TABLE 1

Yield of GRF(1-44)-Ala in Palladium-Promoted Cleavage of Recombinant Chimeric proteins

| Peptide cleaved | palladium(II) complex | Medium | Temp. (° C.) | Time (hr) | Yield (%) |
| --- | --- | --- | --- | --- | --- |
| Leader CH-GRF(1-44)Ala | $Na_2PdCl_4$ | 80% formic acid | 62 | 1.7 | 69.4 |
| Leader CH-GRF(1-44)Ala | $Na_2PdCl_4$ | 80% formic acid | 60 | 4 | 80 |
| Leader CH-GRF(1-44)Ala | $[Pd(NCCH_3)_2(OH_2)_2]^{2+}$ | 80% formic acid | 60 | 4 | 80 |
| Leader CH-GRF(1-44)Ala | $[Pd(dppe)(OH_2)_2]^{2+}$ | 80% formic acid | 60 | 4 | 50 |
| Leader CH-GRF(1-44)Ala | $[Pd(tpp)(OH_2)_2]^{2+}$ | 80% formic acid | 60 | 4 | 40 |
| Leader CH-GRF(1-44)Ala | $[Pd(dppf)(OH_2)_2]^{2+}$ | 80% formic acid | 60 | 4 | 40 |
| Leader CH-GRF(1-44)Ala | $Na_2PdCl_6$ | 80% formic acid | 60 | 4 | 80 |

EXAMPLE 2

Production of a Derivative of Recombinant Human Growth Hormone Releasing Factor (rRF-CH)

Figure 6:
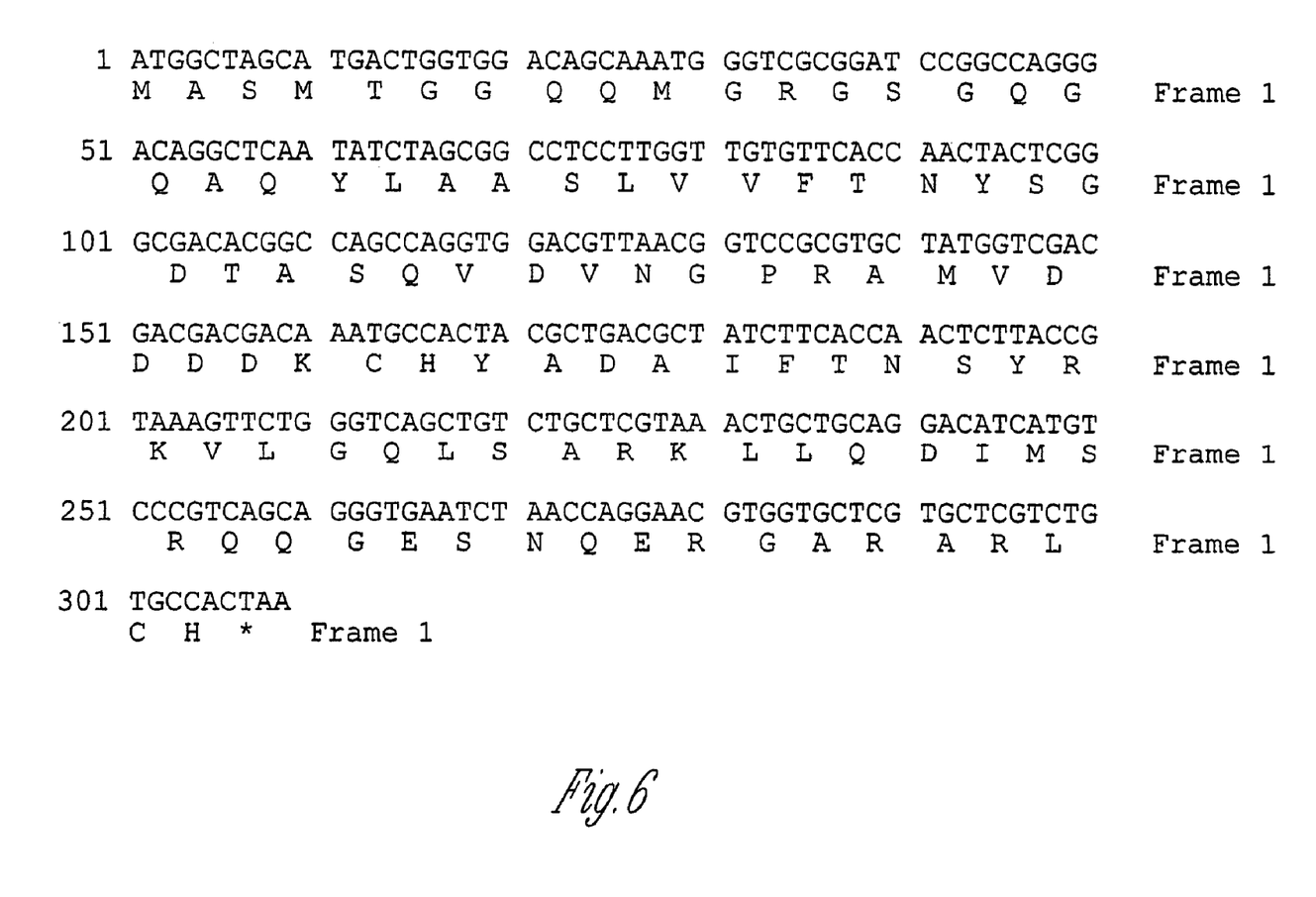
FIG. 6 illustrates the nucleotide (SEQ ID NO:5) and amino acid (SEQ ID NO:6) sequences of the chimeric protein T7tag-Vg-$D_4$K-CH-GRF(1-44)-CH.

1. Expression of the T7tag-Vg-$D_4$K-CH-GRF(1-44)-CH (SEQ ID NO:6) Precursor peptide:

$T_7$tag-Vg-$D_4$KCH-GRF (1-44)-CH (SEQ ID NO:6) FIG. 6) was recombinantly expressed in *E. coli* in accordance with techniques analogous to those disclosed for the expression of rGRF-Ala in Example 1.

2. Solubilization And Cleavage Of T7tag-Vg-$D_4$K-CH-GRF(1-44)-CH (SEQ ID NO:6)

a. Analytical Methods

The following analytical methods and devices were used. The Microsorb-MV $CNC_8$ reverse-phase HPLC method used a Microsorb-MV Cyano-$C_8$ 100 Å, 5 µm, 4.6×150 mm column. The mobile phase system was as follows: A=5% (v/v) acetonitrile, 0.1% (v/v) trifluoroacetic acid; B=95% (v/v) acetonitrile, 0.1% (v/v) trifluoroacetic acid. The gradient used to quantitate the IB sample, (t=0 hours) was as follows: 10-100% B (10.8 min.), 100% B (0.6 min.), 100-10% B (0.6 min.) at 1 ML/min at ambient temperature. The gradient for analysis of the quenched palladium reactions was as follows: 20-30% B (3 min.), 30-40% B (6 min.), 40-100% B (1.5 min), 100-20% B (0.6 min.), 20% B (3 min.) at 1 mL/min at 30° C. Absorbance was monitored from 210-320 mn.

The Waters Symmetry $C_{18}$ reverse-phase HPLC method (or Waters Symmetry $C_{18}$ reverse-phase HPLC method) used a Waters Symmetry $C_{18}$, 100 Å, 3.5 µm, 4.6×150 mm column (Catalog #Wat200632). The mobile phase system was as follows: A=5% (v/v) acetonitrile, 0.1% (v/v) trifluoroacefic acid; B=95% (v/v) acetonitrile, 0.1% (v/v) trifluoroacetic acid. The gradient was 25-33% B (24 min.), 33-60% B (6 min.), 60-90% B (1 min.), 90-25% B (0.5 min.), 25% B (4 min.) at 1 mL/min and 40° C. The absorbance was monitored from 210-320 nm.

The LC/MS method utilized a Waters Symmetry $C_{18}$ column, 100 Å, 3.55 µm, 2.1×150 mm column (Catalog #Wat106005). The mobile phase system was as fallows: A=10% (v/v) acetonitrile, 0.1% (v/v) trifluoroacetic acid; B=60% (v/v) acetonitrile, 0.1% (v/v) trifluoroacetic acid. The gradient was 20-30% B (1 min.), 30-50% B (25 min.), 50-100% B (4 min.), 100-20 % B (1 min.), 20% B (7 min.) at 0.25 mL/min at 40° C. The absorbance was monitored from 210-320 mn. The LCQ Duo MS detector was set to source from 7-19 min. and 24-30 min. The scan event was set from 700-2000 m/z units.

All the reverse-phase HPLC data was collected on a Beckman System Gold HPLC with a photo diode array detector. The LC/MS data was collected on a ThermoQuest Surveyor BPLC with a photo diode array detector and a ThermoQuest Finnigan LCQ Duo mass detector.

During the optimization of the palladium cleavage, it was discovered that the palladium was binding tightly to the-C-terminal Cys-His site. This palladate-GRF complex had an altered spectrum, which inflated the peak area and in turn inflated the cleavage yields. A treatment method for preparing the samples, referred to as the diethyldithiocarbamate(ddtc) treatment, was developed. The treatment was as follows: 50 µL of sample was added to 425 µL of 20 mM ddtc in 8 M urea and allowed to stand at room temperature for five minutes. After the incubation, 25 µL of 100 mM Tris-(2-carboxyethyl) phosphine (TCEP) was added and the sample was centrifuged to remove the yellow palladium-containing precipitate.

EXAMPLE 3

1. Solubilization and cleavage of T7tag-Vg-$D_4$K-CH-GRF (1-44)-CH (SEO ID NO:6)

Figure 2A:
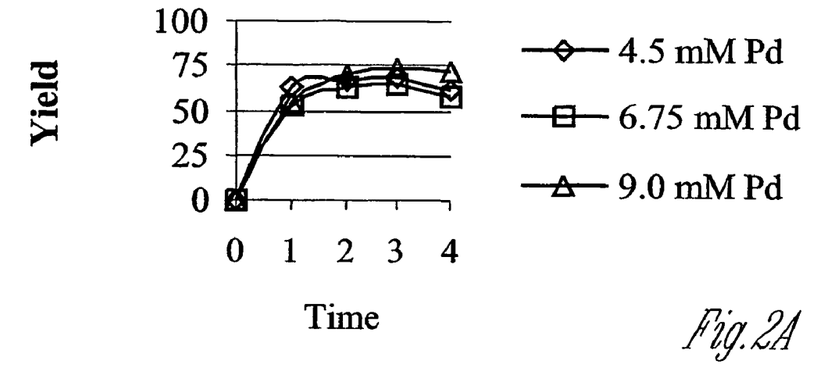
FIG. 2 illustrates the reactivity of the precursor peptide T7tag-Vg-$D_4$K-CH-GRF(1-44)-CH (SEQ ID NO:6) at 60° C. as a function of palladate and formic acid concentration.
Figure 2B:
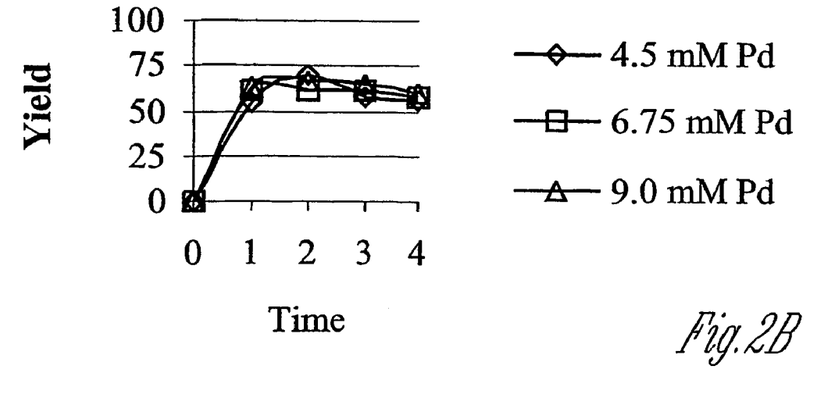
Figure 2C:
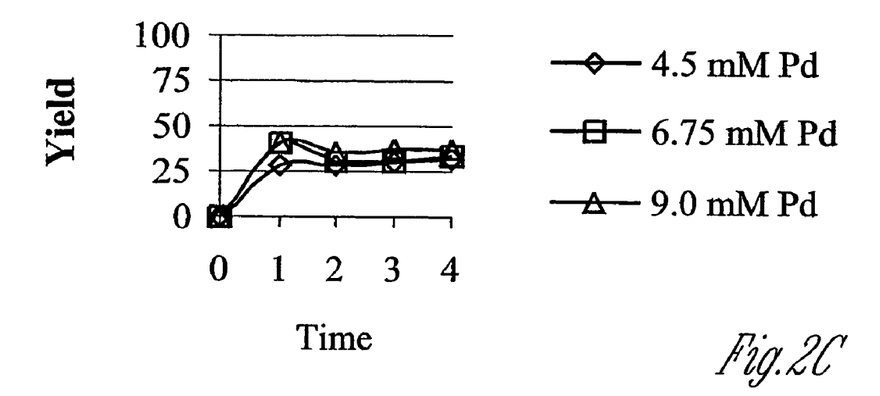

The solubilization and cleavage of T7tag-Vg-$D_4$K-CH-GRF(1-44)-CH ("CH precursor peptide") (SEQ ID NO:6) in 80% formic was studied. A matrix of conditions was designed in which formic acid concentration and tetrachloropalladate concentrations were varied to find optimal conditions of cleavage of this precursor peptide The precursor peptide was homogenized using the plastic probe and the OMNI 5000 high-sheer homogenizer set to solubilize to approximately 5 mg/mL or 0.45 mM precursor peptide. After solubilization, a sample of each solution was taken as a t=0 hr time point which was used to determine the 100% theoretical cleavage yield. Tetrachloropalladate at 4.5, 6.75 and 9 mM was used and the cleavage monitored by HPLC with time points taken every hour. The reactions were done at 60° C. The time points were diluted six-fold with 48 mM thiourea (40 mM final thiourea). All analytical analyses were done as described using the Microsorb-MV $CNC_8$ reverse-phase HPLC method. The results are summarized in FIG. 2. Yields are around 40% in 60% formic with a maximum in one hour but in 80% formic acid yields as high as 75% are achieved. Over the range of tetrachloropalladate concentrations employed (4.5 to 9 mM) there is no appreciable difference in yield.

EXAMPLE 4

Tetrachloropalladate Promoted Cleavage in 75% Formic Acid

Figure 3:
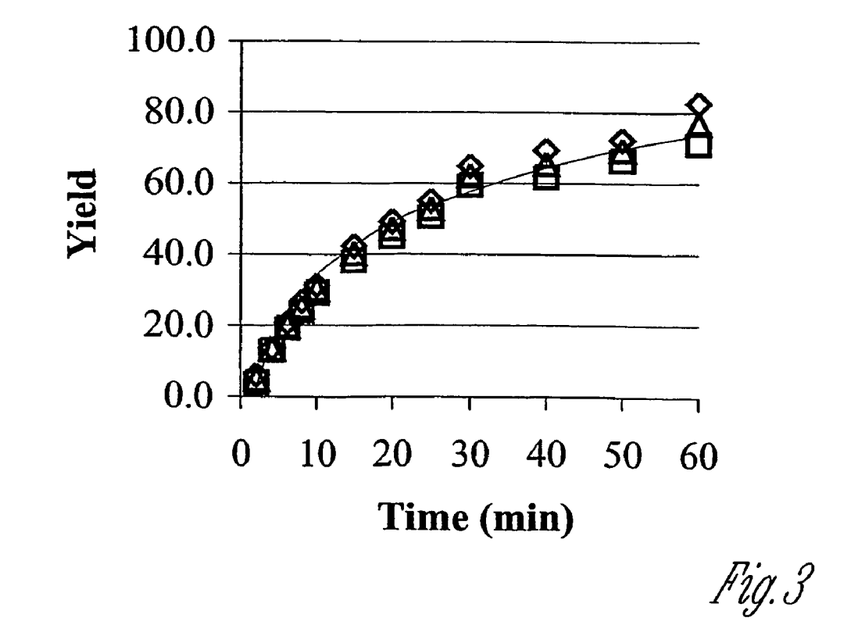
FIG. 3 illustrates the cleavage of T7tag-Vg-$D_4$K-CH-GRF (1-44)-CH (SEQ ID NO:6) by tetrachloropalladate at 60° C. in 75% formic acid.

Tetrachloropalladate promoted cleavage in 75% formic acid was investigated over an hour period at 60° C. The precursor peptide T7tag-Vg-$D_4$K-CH-GRF(1-44)-CH (SEQ ID NO:6) was solubilized into 78% formic acid and diluted to 75% for the reaction. Palladium was added to 4.5 mM from a stock solution. The reaction was at 60° C. for one hour, with time points taken at the following times: 2, 4, 6, 8, 10, 15, 20, 25, 30, 40, 50, and 60 minutes. Each time point was diluted six-fold with 48 mM thiourea. The samples were analyzed using the Microsorb-MV CNC8 reverse-phase HPLC method. FIG. 3 shows a plot of the time course of this reaction showing that in about 60 minutes under these conditions up to 80% cleavage to GRF-CH is obtained. As shown the reactions were done in duplicate and the average yield for the two reactions is plotted as the line. This shows that the cleavage is efficient, rapid and reproducible.

EXAMPLE 5

Inhibition by Chelators

Thiourea is a good chelating reagent to palladium (*The Chemistry of Platinum and Palladium*, F. R. Hartley, Applied Science, 1993, Publishers LTD, London, 1993). Both ethylenediamine and thiourea were added as ligands during the palladium cleavage in 80% formic acid to assess if they might improve the reaction speed or yield by preventing reduction of palladate that accompanies reactions in formic acid. The reactions were prepared and performed using the aforementioned conditions, except that thiourea was added in a 1:1 ratio with palladium in one reaction and ethylenediamine was added in a 2:1 ratio with palladium in another reaction. Each ligand was added from a stock solution. Each reaction was quenched with a six-fold dilution into 0.3 M NaCl and 1.8 mM NASCN (0.25 M and 1.5 mM final). The samples were analyzed using the Microsorb-MV $CNC_8$ reverse-phase HPLC method. These reagents had deleterious effects in that in thiourea the reaction only produced a 5% yield and with ethylenediamine the yield dropped to 55% from that of control that was 83%.

EXAMPLE 6

Production of PTH(1-34)

1. Expression of the Chimeric Protein

Figure 5:
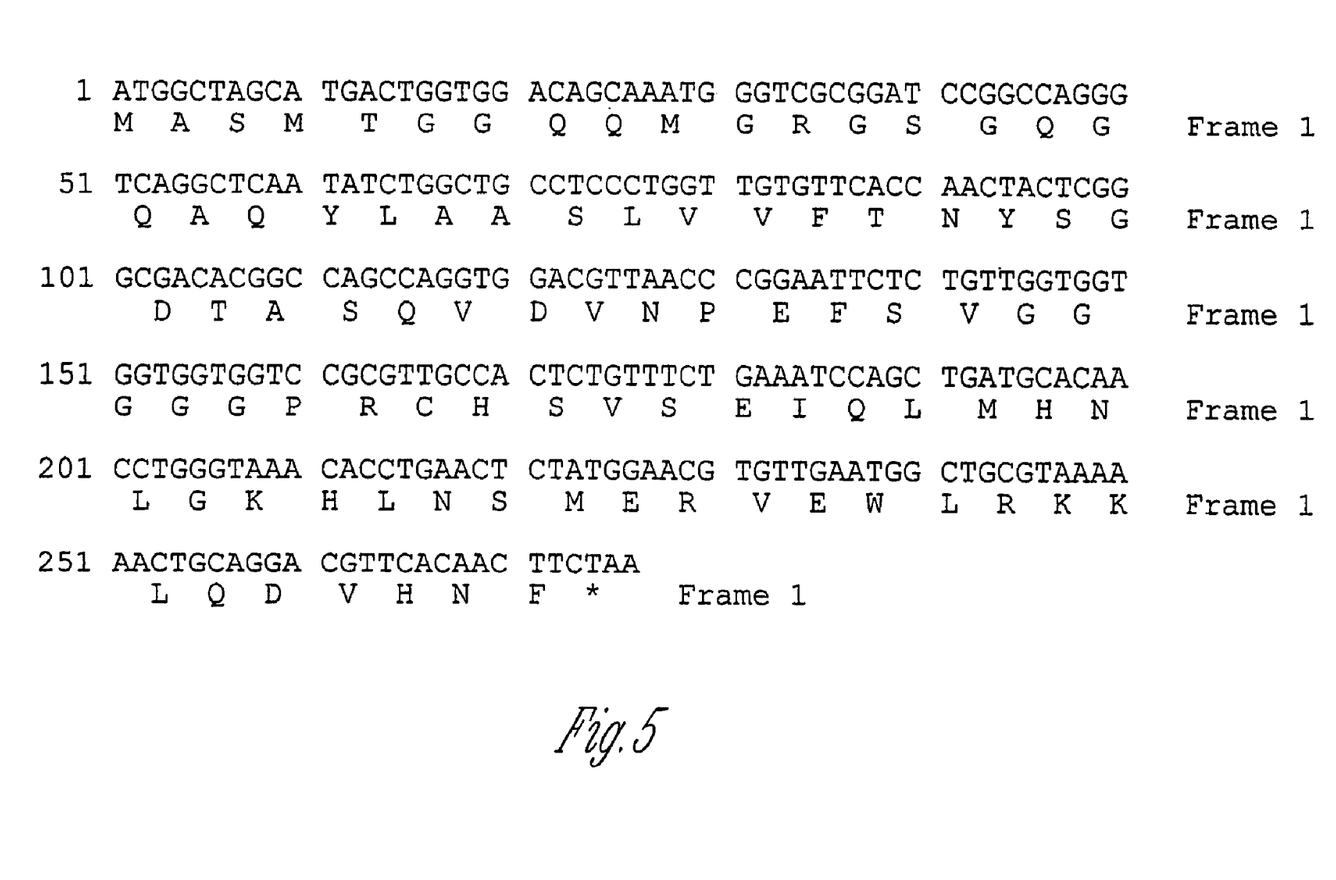
FIG. 5 illustrates the nucleotide (SEQ ID NO:3) and amino acid (SEQ ID NO:4) sequences of the chimeric protein T7tag-Vg-$G_5$PR-CH-PTH (1-34).

DNA encoding PTH(1-34) was cloned downstream of a 10-amino acid leader sequence in a bacterial expression vector to generate T7tag-yg-$G_5$PR-CH-PTH (1-34) (FIG. 5) (SEQ ID NO:4). The expressed chimeric protein is 91 amino acids in length. Inclusion body preparations were obtained from E. coli tranformed with the expression construct essentially as described above for the production of GRF(1-44)CH. Precipitated inclusion bodies were washed by resuspension in water with sonication, centred to obtain a pellet, then dissolved at a concentration of 6 mg/mL in the medium and palladium complex mixtures, as indicted in Table 1.

2. Cleavage of PTH (1-34) Chimeric Protein by Palladium Complexes

A solution of 20 mL containing 5 mg/mL of T7tag-Vg-$G_5$PR-CH-PTH (1-34) (SEQ ID NO:4) inclusion body, 80% formic acid and 5.86 mM sodium tetrachloropalladate was incubated at 60° C. for 240 min. Samples of 200 microliters were taken at times 0, 30, 90, 135, 180, 210, and 240 minutes and diluted 6 fold into 0.6 M NaCl containing 12 mM potassium thiocyanate. Aliquots were filtered through a 0.45 micron filter and examined by reversed phase HPLC using a Vydac RP (4.6×250 mm) 10 micron column with an acetonitrile-water-1% trifluoroacetic acid gradient system. Products were eluted with the following gradient of acetonitrile; 9.5 to 19.4% in 2 min, 19.4 to 29% to 22 min and 29 to 95% in 0.5 min. As the reaction proceeded the appearance of PTH(1-34) was apparent. The reaction was allowed to stand at 4° C. over night then assayed as above. PTH(1-34) was quantitated relative to a standard of PTH(1-34) and it was found that the cleavage yield was 36%. Thus, effective cleavage of the T7tag-Vg-$G_5$PR-CH-PTH (1-34) peptide precursor, like those of GRF had occurred.

These results show rapid and high yield cleavage of PTH (1-34) from chimeric protein-containing inclusion bodies incubated at 60° C. in high concentrations of formic acid with sodium tetrachloropalladate (II).

EXAMPLE 7

Tetrachloropalladate Promoted Hydrolytic Cleavage of Oxidized T7tag-Vg-$D_4$K-CH-GRF(1-44)-A (SEQ ID NO:2) in Formic Acid.

An aged sample of T7tag-Vg-$D_4$K-CH-GRF(1-44)-A (SEQ ID NO:2) was shown to be oxidized to (T7tag-Vg-$D_4$K-CH-GRF(1-44)-A (SEQ ID NO:2))$_2$ by non-reducing gel electrophoresis. The dimer was in roughly a 2:1 ratio compared to the monomer. The mixture was treated with tetrachloropalladate in 86% formic acid for 2 hours at 60° C. The reaction solution was diluted to 10 fold with 25 mM thiourea and 8 M urea followed by centrifugation. The resulting supernatant was analyzed on non-reducing protein gel electrophoresis. The peptide dimer band had disappeared and only a trace amount of unreacted monomer was still observed on the gel. The cleavage yield was about 60%. This experiment shows that even if the Cys residue of the Cys-His cleavage site is in the disulfide state cleavage still occurs.

All publications, patents and patent applications cited herein as well as priority application Ser. No. 60/383,484, filed May 24, 2002 are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic. principles of the invention.

What is claimed is:

1. A palladium-promoted hydrolytic polypeptide cleavage process which selectively cleaves the polypeptide at a Cys-His cleavage site comprising solubilizing the polypeptide in a reaction mixture comprised of a palladium promotor dissolved in a formic acid solvent having a concentration of 50% to 80%, wherein the concentration of the formic acid in the reaction mixture is between about 13 to about 22 molar, wherein the cleavage occurs at the carboxamide bond between the histidine residue and the residue immediately adjacent to the histidine on the C-terminal side.

2. The process of claim 1, wherein the polypeptide is a recombinantly expressed chimeric protein in the form of an inclusion body and the molar ratio of palladium promotor to inclusion body in the reaction mixture is from about 2:1 to about 20:1.

3. The process of claim 2, wherein the molar ratio of palladium promotor to inclusion body in the reaction mixture is from about 2:1 to about 20:1 and the concentration of formic acid is 50 to 80%.

4. The process of claims 1, 2 or 3, wherein the reaction mixture temperature is maintained at about 50° C. to about 70° C.

5. The process of claims 1, 2 or 3, wherein the cleavage reaction proceeds for 0.5 to 6 hours.

6. The process of claim 1, wherein the cleavage site includes a linker, which is N-terminally adjacent to Cys.

7. The process of claim 6, wherein the linker is selected from the group consisting of acidic residues, hydrophobic residues and basic residues inserted in front of a Cys-His sequence.

8. The process of claims 1 or 2, wherein the palladium promoter is a Palladium(II) complex selected from the group consisting of $Na_2PdCl_4$; cis-$[Pd(en)Cl_2]$; cis-$[Pd(bp)Cl_2]$; cis-$[Pd(phen)Cl_2]$; cis-$[Pd(pn)Cl_2]$; cis-$[Pd(pic)Cl_2]$; cis-[Pd (dtco-OH)$Cl_2$; $[Pd(en)(OH_2)_2]^{2+}$, cis-$[Pd(pn)(OH_2)_2]^{2+}$, cis-$[Pd(Pic)(OH_2)_2]^{2+}$-, cis-$[Pd(bp)(OH_2)_2]^{2+}$; cis-$[Pd(phen)(OH_2)_2]^{2+}$, cis-$[Pd(dtco-OH)(OH_2)_2]^{2+}$; and $[Pd(OH_2)_3(OH)](NO_3)$.

9. The process of claim 1, wherein the chimeric protein was expressed recombinantly in host cells and was recovered from the host cells in the form of an inclusion body.

10. The process of claim 9, wherein the peptide is hGRF, the host cells are E. coli and the chimeric protein is T7tag-Vg-$D_4$-CH-GRF (1-44)-Xaa (SEQ ID NO:9), where Xaa is any amino acid.

11. The process of claim 9, wherein the peptide is rPTH, the host cells are E. coli and the chimeric protein is T7tag-Vg-$G_5$PR-CH-PTH(1-34) (SEQ ID NO:4).

12. The process of claims 1 or 2, wherein the formic acid is combined with an inorganic acid selected from the group consisting of HCl, $H_3PO_4$, $H_2SO_4$, or $HClO_4$.

13. The process of claim 9, wherein the palladium promotor is tetrachloropalladate.

14. The process of claims 1, 2, 9 or 13, wherein the palladium promotor is tetrachloropalladate and the molar ratio of tetrachloropalladate to chimeric protein is around 10:1.

15. The process of claim 14, wherein the chimeric protein is T7tag-Vg-$D_4$KCH-GRF(1-44)-CH (SEQ ID NO:6).

16. The process of claim 1, wherein the polypeptide is GLP-1, GLP-2, GRF, PTH, parathyroid hormone related hormone, ACTH, enkephalins, endorphins, exendins, amylins, various opioid peptides, gaegurin 5, gaegurin 6, brevinin 1, a ranatuerin selected from the group consisting of ranatuerin 1 through 9, an esculetin, GIP, glucagon, motilin, a thymopoietin, a thymosin, ubiquitin, serum thymic factor, thymic humoral factor, neurotensin or tuftsin.

17. The process of claim 1, wherein the polypeptide is gastrin, calcitonin, luteinizing-hormone-releasing hormone, pancreatic polypeptide, endothelin, corticotropin releasing factor, neuropeptide Y, atrial naturetic peptide, amylin, galanin, somatostatins, vasoactive intestinal peptide or insulin.

18. The process of claims 16 or 17, wherein the polypeptide is made synthetically.

19. The process of claims 16 or 17, wherein the chimeric protein was expressed recombinantly in host cells and was recovered from the host cells in the form of an inclusion body.

20. The process of claim 19, wherein the host cells are *E. coli*.

21. The process of claims 1 or 9, wherein the cleavage reaction temperature is approximately 60° C.

22. The process of claim 1, wherein the Cys-His cleavage site is present in the polypeptide between a leader sequence and a desired polypeptide sequence.

23. The process of claim 1, wherein the polypeptide comprises a chimeric protein having a molecular weight of between about 400 daltons and about 100,000 daltons.

24. The process of claim 23, wherein the polypeptide comprises repeating units of the chimeric protein.

25. A process for producing a cleaved, deformylated peptide comprising:
   (a) cleaving a chimeric protein comprised of a leader sequence joined by a Cys-His cleavage site to the N-terminus of the peptide by solubilizing the chimeric protein in a reaction mixture comprised of a palladium promotor dissolved in formic acid solvent having a concentration of 50 to 80%, wherein the cleavage occurs at the carboxamide bond between the histidine residue and the residue immediately adjacent to the histidine on the C-terminal side; and
   (b) deformylating the peptide cleaved in step (a) by removing the formic acid Solvent from the reaction product of step (a) and reacting the resultant reaction product containing cleaved peptide with a mixture of 0 to 2 M glycine and 0 to 100 mM hydroxylamine at a pH of 6 to 9 or by incubating the formylated peptide for 4 to 16 hours in a dilute acid.

26. The process of claim 25, wherein the chimeric protein was expressed recombinantly in host cells and was recovered from the host cells in the form of an inclusion body.

27. The process of claim 22, wherein the reaction mixture temperature is maintained at about 50° C. to about 70° C.

28. The process of claim 27, wherein the cleavage reaction proceeds for 0.5 to 6 hours.

29. The process of claim 27, wherein the cleavage site includes a linker, which is adjacent to Cys.

30. The process of claim 27, wherein the linker is selected from the group consisting of acidic residues, hydrophobic residues and basic residues may be inserted in front of a Cys-His sequence.

31. The process of claim 27, wherein the formic acid is combined with one or more palladium complexes with ligands selected from the group consisting of ethylenediamine; propylenediamine; 2-aminomethyl pyridine; 2(2-aminoethyl) pyridine; 2(2-methylaminoethyl)pyridine; 2,2'-bypyridyl; 1,10-phenanthroline: 3-hydroxy-2 (dimethylaminomethyl)pyridine; 3-hydroxy-1, 5-dithiacyclooctane; 3,6-dithiaoctane-1,8-diol; 1,2-diphenylphosphineethane; triphenylphosphine; diphenylphosphineferrocene; and diethylenetriamine.

32. The process of claim 27, wherein the palladium promoter is a Palladium(II) complex selected from the group consisting of $Na_2PdCl_4$; cis-[Pd(en)$Cl_2$]; cis-[Pd(bp)$Cl_2$]; cis-[Pd(phen)$Cl_2$]; cis-[Pd(pn)$Cl_2$]; cis-[Pd(pic)$Cl_2$]; cis-[Pd(dtco-OH)$Cl_2$]; cis-[Pd(en)(OH$_2$)$_2$]$^{2+}$, cis-[Pd(Pn)(OH$_2$)$_2$]$^{2+}$, cis-[Pd(pic)(OH$_2$)$_2$]$^{2+}$, cis-[Pd(bp)(OH$_2$)$_2$]$^{2+}$; cis-[Pd(phen)(OH$_2$)$_2$]$^{2+}$; cis-[Pd(dtco-OH)(OH$_2$)$_2$]$^{2+}$, And [Pd(OH$_2$)$_3$(OH)](NO$_3$) or a palladium (IV) complex including $Na_2PdCl_6$.

33. The process of claim 26, wherein the molar ratio of palladium promotor to inclusion body in the reaction mixture is from about 2:1 to about 20:1.

34. The process of claim 26, wherein the peptide is rGRF, the host cells are *E. coli* and the chimeric protein is T7tag-Vg-D$_4$-CH-GRF(1-44)-CH (SEQ ID NO:6).

35. The process of claim 27, wherein the formic acid is combined with an inorganic acid selected from the group consisting of HCl, $H_3PO_4$, $H_2SO_4$, $HClO_4$, or $HClO_4$.

36. The process of claim 27, wherein the palladium promotor is tetrachloropalladate.

37. The process of claims 27 or 35, wherein the palladium promotor is tetrachloropalladate and the molar ratio of tetrachloropalladate to chimeric protein is around 10:1.

38. The process of claim 37, wherein the chimeric protein is T7tag-Vg-D$_4$K-CH-GRF(1-44)-CH (SEQ ID NO:6).

39. The process of claim 27, wherein the peptide is GLP-1, GLP-2, GRF, PTH, parathyroid hormone releasing hormone, ACTH, enkephalins, endorphins, exendins, amylins, various opioid peptides, gaegurin 5, gaegurin 6, brevinin 1, a ranatuerin selected from the group consisting of ranatuerin 1 through 9, an esculetin, GIP, glucagon, motilin, a thymopoietin, a thymosin, ubiquitin, serum thymic factor, thymric humoral factor, neurotensin or tuftsin.

40. The process of claim 27, wherein the peptide is gastrin, calcitonin, luteinizing-hormone-releasing hormone, pancreatic polypeptide, endothelin, corticotropin releasing factor, neuropeptide Y, atrial naturetic peptide, amylin, galanin, somatostatins, vasoactive intestinal peptide or insulin.

41. The process of claims 39 or 40, wherein the chimeric protein is made synthetically.

42. The process of claims 39 or 40, wherein the chimeric protein was expressed recombinantly in host cells and was recovered from the host cells in the form of an inclusion body.

43. The process of claim 42, wherein the host cells are *E. coli*.

44. The process of claims 27 or 43, wherein the cleavage reaction temperature is approximately 60° C.

45. The process of claims 27 or 43, wherein the cleaved, deformylated peptide produced in step (b) is recovered by ultrafiltration, filtration or ion-exchange chromatography or reverse phase chromatography or any means of chromatography.

46. The process of claim 1 wherein the Cys of the Cys-His cleavage site is in the oxidized disulfide state.

47. A process for producing a cleaved, deformylated peptide comprising:
   (a) cleaving a chimeric protein comprised of a leader sequence joined by a Cys-His cleavage site to the N-terminus of the peptide by solubilizing the chimeric protein in a reaction mixture comprised of a palladium promotor dissolved in formic acid solvent having a concentration of 50 to 80%; and
   (b) deformylating the peptide cleaved in step (a) by removing the formic acid solvent from the reaction product of step (a) and reacting the resultant reaction product containing cleaved peptide with a mixture of 0 to 2 M glycine and 0 to 100 mM hydroxylamine at a pH of 6 to 9 or by incubating the formylated peptide for 4 to 16 hours in a dilute acid.

* * * * *

UNITED STATES PATENT AND TRADEMARK OFFICE
CERTIFICATE OF CORRECTION

PATENT NO. : 7,592,432 B2  Page 1 of 1
APPLICATION NO. : 10/997822
DATED : September 22, 2009
INVENTOR(S) : Holmquist et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1126 days.

Signed and Sealed this

Twenty-first Day of September, 2010

David J. Kappos
*Director of the United States Patent and Trademark Office*

SEQUENCE LISTING

```
<160> NUMBER OF SEQ ID NOS: 9

<210> SEQ ID NO 1
<211> LENGTH: 306
<212> TYPE: DNA
<213> ORGANISM: Artificial Sequence
<220> FEATURE:
<223> OTHER INFORMATION: Nucleotide sequence of a synthetic chimeric
      protein.

<400> SEQUENCE: 1
atggctagca tgactggtgg acagcaaatg ggtcgcggat ccggccaggg acaggctcaa      60
tatctagcgg cctccttggt tgtgttcacc aactactcgg gcgacacggc cagccaggtg     120
gacgttaacg gtccgcgtgc tatggtcgac gacgacgaca aatgccacta cgctgacgct     180
atcttcacca actcttaccg taaagttctg ggtcagctgt ctgctcgtaa actgctgcag     240
gacatcatgt cccgtcagca gggtgaatct aaccaggaac gtggtgctcg tgctcgtctg     300
gcataa                                                                306
```

<210> SEQ ID NO 2
<211> LENGTH: 101
<212> TYPE: PRT
<213> ORGANISM: Artificial Sequence
<220> FEATURE:
<223> OTHER INFORMATION: Amino acid sequence of a synthetic chimeric protein.

<400> SEQUENCE: 2

Met Ala Ser Met Thr Gly Gly Gln Gln Met Gly Arg Gly Ser Gly Gln
1               5                   10                  15

Gly Gln Ala Gln Tyr Leu Ala Ala Ser Leu Val Val Phe Thr Asn Tyr
            20                  25                  30

Ser Gly Asp Thr Ala Ser Gln Val Asp Val Asn Gly Pro Arg Ala Met
        35                  40                  45

Val Asp Asp Asp Lys Cys His Tyr Ala Asp Ala Ile Phe Thr Asn
    50                  55                  60

Ser Tyr Arg Lys Val Leu Gly Gln Leu Ser Ala Arg Lys Leu Leu Gln
65                  70                  75                  80

Asp Ile Met Ser Arg Gln Gln Gly Glu Ser Asn Gln Glu Arg Gly Ala
                85                  90                  95

Arg Ala Arg Leu Ala
            100

<210> SEQ ID NO 3
<211> LENGTH: 276
<212> TYPE: DNA
<213> ORGANISM: Artificial Sequence
<220> FEATURE:
<223> OTHER INFORMATION: Nucleotide sequence of a synthetic chimeric protein.

<400> SEQUENCE: 3
atggctagca tgactggtgg acagcaaatg ggtcgcggat ccggccaggg tcaggctcaa      60
tatctggctg cctccctggt tgtgttcacc aactactcgg gcgacacggc cagccaggtg     120
gacgttaacc cggaattctc tgttggtggt ggtggtggtc cgcgttgcca ctctgtttct     180
gaaatccagc tgatgcacaa cctgggtaaa cacctgaact ctatggaacg tgttgaatgg     240
ctgcgtaaaa aactgcagga cgttcacaac ttctaa                               276

<210> SEQ ID NO 4
<211> LENGTH: 91
<212> TYPE: PRT
<213> ORGANISM: Artificial Sequence
<220> FEATURE:
<223> OTHER INFORMATION: Amino acid sequence of a synthetic chimeric protein.

<400> SEQUENCE: 4

Met Ala Ser Met Thr Gly Gly Gln Gln Met Gly Arg Gly Ser Gly Gln
1               5                   10                  15

Gly Gln Ala Gln Tyr Leu Ala Ala Ser Leu Val Val Phe Thr Asn Tyr
            20                  25                  30

Ser Gly Asp Thr Ala Ser Gln Val Asp Val Asn Pro Glu Phe Ser Val
        35                  40                  45

Gly Gly Gly Gly Gly Pro Arg Cys His Ser Val Ser Glu Ile Gln Leu
    50                  55                  60

Met His Asn Leu Gly Lys His Leu Asn Ser Met Glu Arg Val Glu Trp
65                  70                  75                  80

Leu Arg Lys Lys Leu Gln Asp Val His Asn Phe
                85                  90

-continued

<210> SEQ ID NO 5
<211> LENGTH: 309
<212> TYPE: DNA
<213> ORGANISM: Artificial Sequence
<220> FEATURE:
<223> OTHER INFORMATION: Nucleotide sequence of a synthetic chimeric
      protein.

<400> SEQUENCE: 5

```
atggctagca tgactggtgg acagcaaatg ggtcgcggat ccggccaggg acaggctcaa      60
tatctagcgg cctccttggt tgtgttcacc aactactcgg gcgacacggc cagccaggtg     120
gacgttaacg gtccgcgtgc tatggtcgac gacgacgaca atgccacta cgctgacgct     180
atcttcacca actcttaccg taaagttctg ggtcagctgt ctgctcgtaa actgctgcag     240
gacatcatgt cccgtcagca gggtgaatct aaccaggaac gtggtgctcg tgctcgtctg     300
tgccactaa                                                             309
```

<210> SEQ ID NO 6
<211> LENGTH: 102
<212> TYPE: PRT
<213> ORGANISM: Artificial Sequence
<220> FEATURE:
<223> OTHER INFORMATION: Amino acid sequence of a synthetic chimeric
      protein.

<400> SEQUENCE: 6

Met Ala Ser Met Thr Gly Gly Gln Gln Met Gly Arg Gly Ser Gly Gln
1               5                   10                  15
Gly Gln Ala Gln Tyr Leu Ala Ala Ser Leu Val Val Phe Thr Asn Tyr
            20                  25                  30
Ser Gly Asp Thr Ala Ser Gln Val Asp Val Asn Gly Pro Arg Ala Met
        35                  40                  45
Val Asp Asp Asp Lys Cys His Tyr Ala Asp Ala Ile Phe Thr Asn
    50                  55                  60
Ser Tyr Arg Lys Val Leu Gly Gln Leu Ser Ala Arg Lys Leu Leu Gln
65                  70                  75                  80
Asp Ile Met Ser Arg Gln Gln Gly Glu Ser Asn Gln Glu Arg Gly Ala
                85                  90                  95
Arg Ala Arg Leu Cys His
            100

<210> SEQ ID NO 7
<211> LENGTH: 7
<212> TYPE: PRT
<213> ORGANISM: Artificial Sequence
<220> FEATURE:
<223> OTHER INFORMATION: A synthetic amino acid sequence of an
      illustrative amino acid sequence.

<400> SEQUENCE: 7

Ala Ala Cys His Gly Gly Gly
1               5

<210> SEQ ID NO 8
<211> LENGTH: 4
<212> TYPE: PRT
<213> ORGANISM: Artificial Sequence
<220> FEATURE:
<223> OTHER INFORMATION: A synthetic amino acid sequence of an
      illustrative amino acid sequence.

<400> SEQUENCE: 8

Ala Ala Cys His
1

<210> SEQ ID NO 9

-continued

```
<211> LENGTH: 101
<212> TYPE: PRT
<213> ORGANISM: Artificial Sequence
<220> FEATURE:
<223> OTHER INFORMATION: Amino acid sequence of a synthetic chimeric
      protein.
<220> FEATURE:
<221> NAME/KEY: SITE
<222> LOCATION: 101
<223> OTHER INFORMATION: Xaa = any amino acid.

<400> SEQUENCE: 9

Met Ala Ser Met Thr Gly Gly Gln Gln Met Gly Arg Gly Ser Gly Gln
1               5                   10                  15

Gly Gln Ala Gln Tyr Leu Ala Ala Ser Leu Val Val Phe Thr Asn Tyr
            20                  25                  30

Ser Gly Asp Thr Ala Ser Gln Val Asp Val Asn Gly Pro Arg Ala Met
        35                  40                  45

Val Asp Asp Asp Asp Lys Cys His Tyr Ala Asp Ala Ile Phe Thr Asn
    50                  55                  60

Ser Tyr Arg Lys Val Leu Gly Gln Leu Ser Ala Arg Lys Leu Leu Gln
65                  70                  75                  80

Asp Ile Met Ser Arg Gln Gln Gly Glu Ser Asn Gln Glu Arg Gly Ala
                85                  90                  95

Arg Ala Arg Leu Xaa
            100
```